(12) United States Patent
Malmstrom et al.

(10) Patent No.: US 6,531,708 B1
(45) Date of Patent: Mar. 11, 2003

(54) OPTICAL BUBBLE DETECTION SYSTEM

(75) Inventors: James A. Malmstrom, Kaysville, UT (US); Kent F. Beck, Layton, UT (US); Scott D. Miles, Sandy, UT (US)

(73) Assignee: Zevex, Inc., DE (US)

( * ) Notice: Subject to any disclaimer, the term of this patent is extended or adjusted under 35 U.S.C. 154(b) by 0 days.

(21) Appl. No.: 09/836,840

(22) Filed: Apr. 16, 2001

(51) Int. Cl.$^7$ ................................................. G01N 15/06
(52) U.S. Cl. ...................................... 250/573; 250/574
(58) Field of Search ................................ 250/573, 574, 250/575, 576; 356/246, 436, 440, 442

(56) References Cited

U.S. PATENT DOCUMENTS

| | | |
|---|---|---|
| 3,090,222 A | 5/1963 | Akaboshi et al. |
| 3,450,476 A | 6/1969 | Rando |
| 4,193,004 A | 3/1980 | Lobdell et al. |
| 4,312,341 A | 1/1982 | Zissimopoulos et al. |
| 4,559,454 A | 12/1985 | Kramer |
| 4,631,529 A | 12/1986 | Zeitz |
| 4,829,448 A | 5/1989 | Balding et al. |
| 4,833,918 A | 5/1989 | Jean et al. |
| 4,881,487 A | 11/1989 | Moore |
| 4,884,065 A | 11/1989 | Crouse et al. |
| 4,908,676 A | 3/1990 | Bedell et al. |
| 4,920,336 A | 4/1990 | Meijer |
| 4,998,022 A | 3/1991 | Tregay |
| 5,074,659 A | 12/1991 | Suzuki et al. |
| 5,116,759 A | 5/1992 | Klainer et al. |
| 5,260,665 A | 11/1993 | Goldberg et al. |
| 5,305,237 A | 4/1994 | Dalrymple et al. |
| 5,422,495 A | 6/1995 | Cohn |
| 5,499,077 A | 3/1996 | Endo et al. |
| 5,534,708 A | 7/1996 | Ellinger et al. |
| 5,557,368 A | 9/1996 | Endo et al. |
| 5,672,887 A | 9/1997 | Shaw et al. |
| 5,680,111 A | 10/1997 | Danby et al. |
| 5,764,356 A | 6/1998 | Iwase et al. |

FOREIGN PATENT DOCUMENTS

EP  0 261 860 A2  9/1987

Primary Examiner—Georgia Epps
Assistant Examiner—Richard Hanig
(74) Attorney, Agent, or Firm—Morriss, Bateman, O'Bryant & Compagni

(57) ABSTRACT

An optical sensor includes a sample cell through which a fluid flows, an optical sensor formed by an optical emitter and an optical detector. The sample cell and the optical sensor use light refraction to determine the presence and size of a bubble passing through the sample cell. A housing may also be included to provide better control over light refraction and to protect the optical sensor.

69 Claims, 8 Drawing Sheets

OPTICAL BUBBLE DETECTION SYSTEM

BACKGROUND OF THE INVENTION

1. Field of the Invention

The present invention relates to systems for administering solutions to patients in such a manner as to decrease the risk that air bubbles will be inadvertently provided to the patient. More specifically, the present invention relates to a system for optically detecting bubbles in solution being provided to a patient.

2. State of the Art

Parenteral and Enteral feeding systems are used to provide solutions to patients. In parenteral systems, solutions such as balanced saline solutions are administered to the patient's circulatory system. Enteral feeding systems are provided for patients who, for one reason or another, are unable to eat for themselves.

One common concern with both parenteral and enteral feeding systems is that it is undesirable for large quantities of air to be provided with the solution. In enteral systems, excessive air may irritate the digestive system of the patient and complicate other medical conditions. Additionally, the air can render the volumetric calculations of the enteral feeding pump inaccurate.

In parenteral applications, the risk can be much greater. While air in a parentral infusion line is undesirable, large quantities of air can cause serious problems in the vascular system. In extreme cases, excessive air can even cause death of the patient. Thus, it is critical in parenteral application that air not be delivered to the patient's vascular system.

In addition to the health concerns posed by the air being released into the patient's body, the presence of air in the parenteral or enteral feeding tube also means that the desired solution is not being delivered to the patient. Each cubic centimeter of air is a cubic centimeter of enteral feeding solution, medication, etc. which is not delivered to the patient. Without being able to detect the quantity of air passing through the system, the system is unable to accurately determine the actual amount of solution which has been delivered to the patient. Over a prolonged period of time, even modest amounts of air passing through the system can cause significant disparities in the amount of solution the system indicates to be delivered and the actual amount delivered.

There are numerous mechanisms available for detecting air in liquid passing through a tube. Many of these mechanisms provide marginal accuracy or are complex to use. Others, while relatively accurate, require considerably more power draw than is necessary. Yet other air detectors do not provide an inherent integrity check to prevent failure of the sensor from giving erroneous information regarding air in the conduit.

While all of the above are disadvantageous, a principle disadvantage of most air detectors which are used in enteral feeding pumps and the like is the cost. Most enteral feeding pumps utilize ultrasonic sensors to check for bubbles. Such sensors, however, can cost fifty times or more the cost of an optical sensor.

Thus, there is a need for an improved sensor for determining the presence of bubbles, which is less expensive, and which is easy to operate.

SUMMARY OF THE INVENTION

It is an object of the present invention to provide an improved sensor for detecting bubbles in a conduit;

It is another object of the present invention to provide such a sensor which is easy to make and use.

It is yet another object of the present invention to provide such a sensor which utilizes refraction of light to determine the presence of air within the conduit.

It is still another object of the present invention to provide such an optical sensor which is relatively inexpensive.

The above and other objects of the invention are realized in specific illustrated embodiments of an optical air/liquid sensing system which utilizes a sample cell. The sample cell has a pair of sidewalls which refract light into the liquid in the conduit at such an angle that the light passes out of the sample cell in a first direction when no air is present in the conduit, and in a second direction when air is present in the conduit.

The sample cell is disposed between an optical emitter and an optical detector. Light is emitted from the optical emitter and is refracted as it passes through the sample cell. The presence of air within the sample cell changes the refraction of light, thereby changing the light received by the optical detector. It should be appreciated that, as used herein, the term light is not limited to electromagnetic radiation in the spectrum visible to humans. To the contrary, a preferred embodiment of the invention utilizes infrared radiation.

In accordance with one aspect of the present invention, the amount of air in the conduit affects the amount of light refracted in the second direction. The amount of light refracted into the first direction versus the amount refracted in the second direction indicates the relative amount of air in the conduit.

In accordance with another aspect of the invention, the sample cell is configured and disposed to always allow some light to pass through the sample cell and to be received by the optical detector. If no light is detected by the optical detector, the system is readily able to determine that the system has failed.

In accordance with another aspect of the invention, the sample cell is situated so that all of the light emitted from the optical emitter does not reach the optical detector. Thus, if the optical detector indicates that nearly all of the light emitted from the optical detector has been received, the optical sensor system can readily determine that the sample cell is not properly loaded between the optical emitter and optical detector of the sensor.

In accordance with another aspect of the invention, the exterior of the sample cell is triangular. The shape of the sample cell regulates the flow of light through the sample cell and thereby directs light to the optical detector depending on whether air is present in the conduit.

In accordance with still yet another aspect of the present invention, a housing is provided and spaced apart from the sample cell by an air channel. As with the shape of the sample cell, the housing helps to direct light through the sample cell at a desired angle to facilitate the determination of whether air is present in the conduit in the sample cell.

Preferably, the housing is formed of a similar material to the sample cell and is disposed at an angle parallel to the sidewalls of the sample cell. This provides for the refraction of light at desired angles through the sample cell.

In accordance with another aspect of the present invention, a sample cell container is provided with a channel disposed therein. Properly mounting a flexible tube in the channel causes the tube to form first and second sidewalls which are disposed at desired angles to refract light in one direction when a solution is present, and to refract light in second direction, i.e. toward an optical signal detector, when the conduit is filled with air.

In a preferred embodiment of the invention, the sample cell has sidewalls which are disposed at an angle of between about 45 and 100 degrees relative to one another are disposed at the same acute angle relative to a plane extending from the optical signal emitter and the optical signal detector. More preferably, the two sidewalls are disposed at an angle of 60 degrees from one another and are disposed at the same relative acute angle from a horizontal or other plane passing through the sample cell from the optical signal emitter and the optical signal detector. By same angle it is meant that each sidewall has a similar acute angle from the plane, although they are in opposite directions.

In accordance with another aspect of the invention, it has been found that the sample cell can be used to determine the presence of air so long as the sample cell wall is less than normal from the plane along which the light is omitted. The closer the sample cell wall is to normal, however, the further away the optical sensor components must be from the sample cell wall. Additionally, the positions of the optical signal emitter and the optical signal detector can be adjusted to ensure light is refracted to the optical sensor when air is present, but not when liquid is present, or vice versa.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
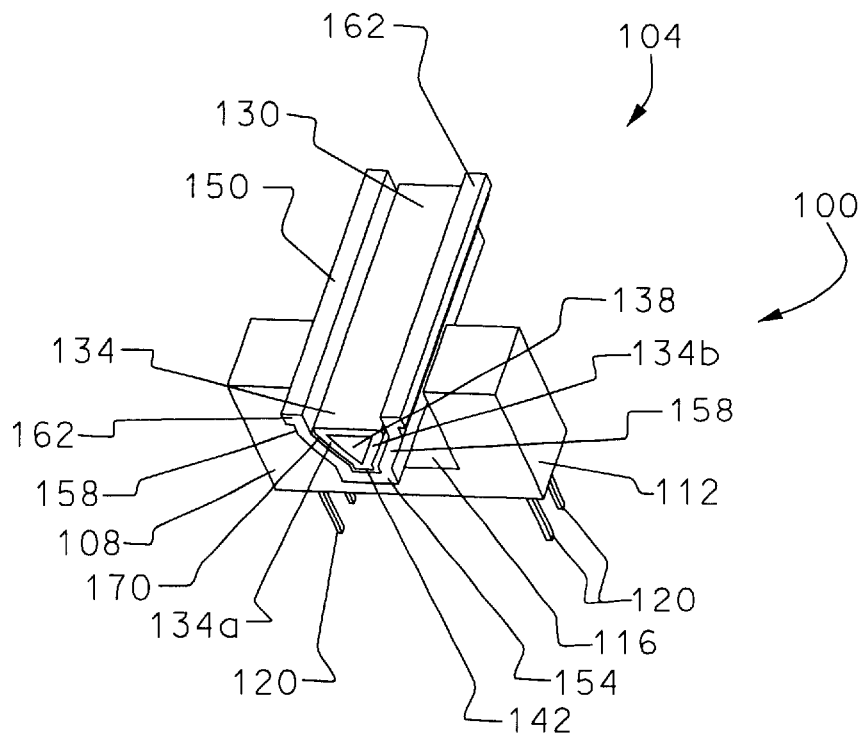
FIG. 1 shows a perspective view of an optical sensing system made in accordance with the principles of the present invention.

Referring to FIG. 1, there is shown a perspective view of an optical sensor system, generally indicated at 100, made in accordance with the principles of the present invention. The optical sensor system 100 includes an optical sensor, generally indicated at 104. The optical sensor 104 has an optical emitter portion 108 which emits light, and an optical detector portion 112 which detects light emitted by the optical detector and generates a voltage that is proportional to the amount of light received. The optical emitter portion 108 and the optical detector portion 112 define a cavity 116 through which the light travels between the two portions. (Those of skill in the art will appreciate that the optical sensor 104 can be made of a paired emitter and detector, or could be formed from two discrete parts.)

The optical sensor 104 further includes a plurality of leads 120 which are used to send and receive electrical signals from the enteral feeding pump with which the optical sensor is associated. Those skilled in the art will appreciate that optical sensors which function in such a manner are inexpensive and readily available.

Positioned to extend through the cavity 116 in the optical sensor 104 is a sample cell 130. The sample cell 130 includes a sample cell wall 134 which defines a conduit 138. In a presently preferred embodiment, the sample cell wall 134 defines a triangular conduit. Most preferably the sample cell wall 134 forms a conduit which, in cross-section, is an inverted equilateral triangle. The sample cell wall 134 also preferably forms a base 142 disposed at the bottom tip of the triangle.

Disposed adjacent to and extending along the sample cell 130 is a housing 150. The housing 150 has a base portion 154 which preferably extends horizontally, a pair of sidewalls 158 which extend upwardly and outwardly, and an upper flange portion 162. The respective sidewalls 158 of the housing 150 preferably are disposed in parallel to the respective side walls 134a and 134b of the sample cell wall 134. Depending on the plastics used, the angle of the sidewalls 134a, 134b and 158 will preferably be between 45 and 100 degrees. Most preferably, they are disposed at an angle of 60 degrees from one another and from a plane along which light would flow uninterrupted between the optical signal emitter 108 and the optical signal detector 112.

The housing 150 and the sample cell 130 are spaced apart from one another and define an air chamber 170 therebetween. The housing 150 serves several purposes. First, the housing 150 prevents water or other liquids from getting into the cavity 116 where it could damage the optical sensor 104. Second, the housing 150 is designed so that even if water were to fill the air chamber 170 between the housing and the sample cell 130, the flow-path of light indicating the presence of liquid or air would be consistent.

Figure 2A:
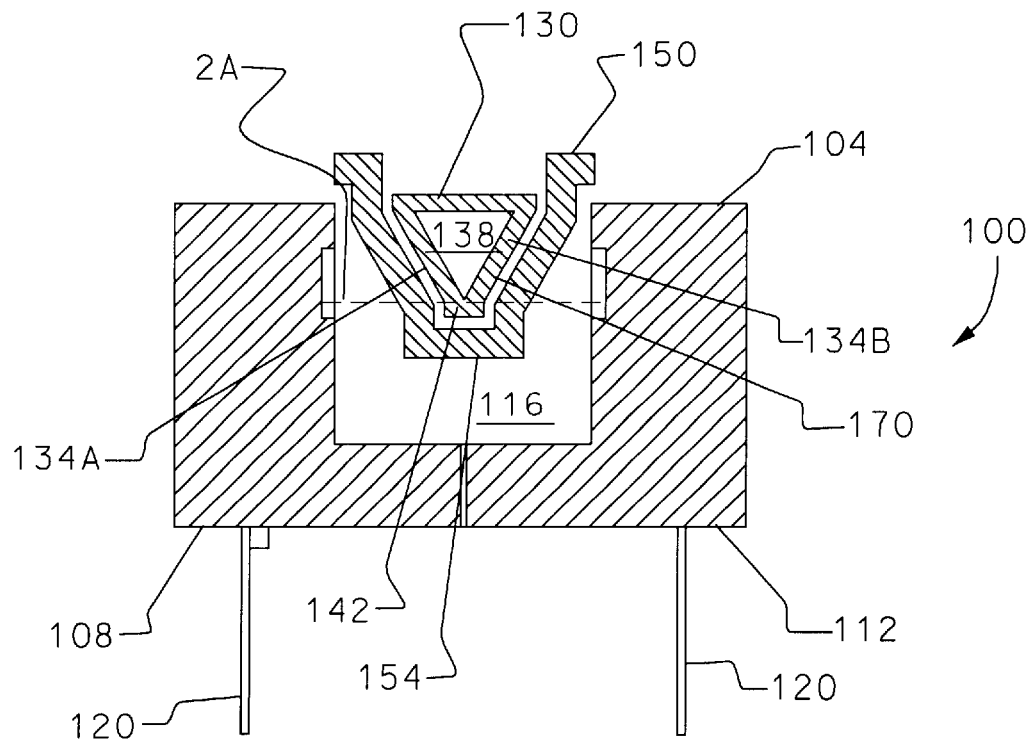
FIG. 2A shows a cross-sectional view of the optical sensing system shown in FIG. 1.

Turning now to FIG. 2A, there is shown a cross-sectional view of the sample cell 130 disposed in cavity 116 between the optical emitter 108 and the optical detector 112 of the optical sensor 104. The housing 150 is disposed in parallel and spaced away from the sample chamber 130 to form the air chamber 170.

As shown, the sample cell 130 is preferably formed by a three part sample cell wall 134 defining a triangular conduit 138. Most preferably, the conduit has a cross-section which is an inverted equilateral triangle. In such a configuration, the two sidewalls 134a and 134b of the sample cell wall 134 are offset from one another sixty degrees. The two sidewalls are also offset from the horizontal plane 2A—2A at an angle of sixty degrees. The horizontal plane 2A—2A represents the plane along which light passing directly from the optical signal emitter 108 to the optical signal detector 112 would pass.

It has been found that such an angular arrangement provides a light flow pattern which readily facilitates the determination if there is air in the sample cell 130 and the relative amount of air present. As will be explained in additional detail below, having the sidewalls disposed at corresponding angles between 47–70 degrees and preferably 60 degrees allows light to be conveniently refracted in one direction if the conduit has liquid therein, and in a second direction, back toward the plane 2A—2A when the conduit is filled with air.

Disposed at the bottom of the sample cell 130 is a base portion 142 which extends horizontally (i.e. parallel with the plane 2A—2A) a short distance, rather than forming a point similar to an inverted equilateral triangle. The base portion 142 allows a certain amount of light to pass through the sample cell 130 and to be received by the optical detector 112 regardless of whether there is air or water in the conduit 138 of the sample cell. This forms an inherent integrity check, as the lack of any detected signal will mean the optical emitter 108 is not working and the optical sensor 104 must be replaced.

Figure 2B:
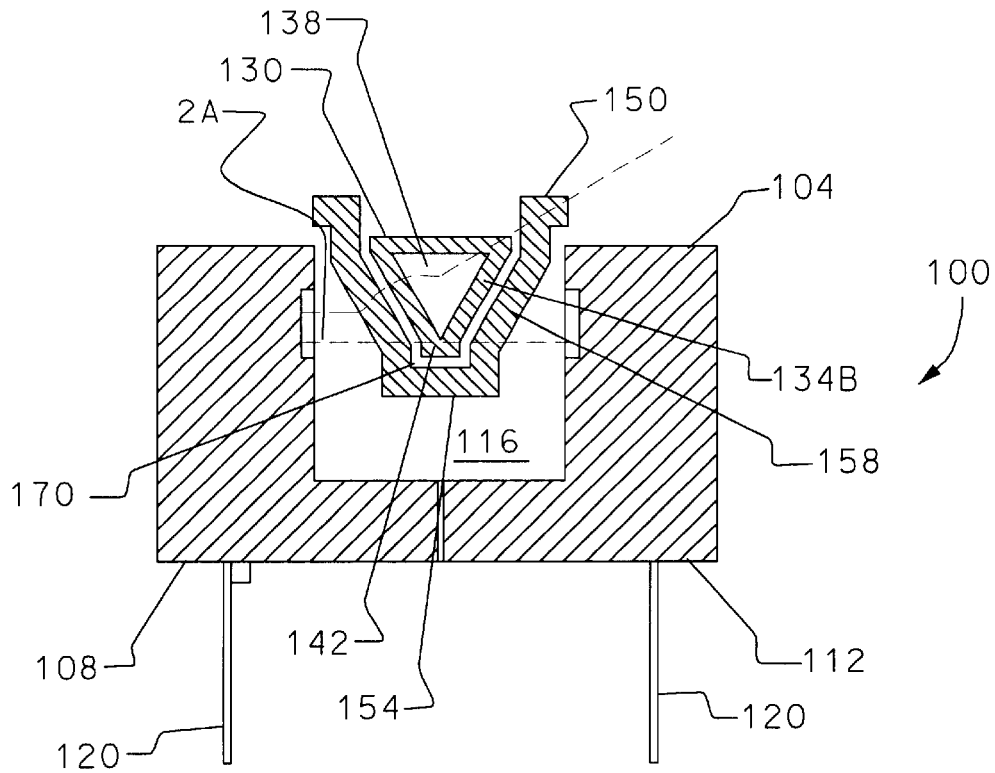
FIG. 2B shows the cross-section view of the optical sensing system shown in FIG. 2A with a conduit of the sample cell filled with liquid.

The housing 150 is positioned to both protect the optical sensor 104 from being damaged by water, etc., and to assist in the flow of light through the sample cell 130. As shown in FIG. 2B, the light from the optical emitter 108 refracts as it passes into and out of the housing 150. It refracts again as it passes into the sample cell wall 134a.

If water or some other translucent solution is present in the conduit 138, the water refracts to a very small degree as it passes from the sample cell wall 134a into the liquid. This is because the refraction index of the plastic which forms the sample cell wall 134 and the refraction index of the liquid is very similar.

Due to the similarities in the indices of refraction, the majority of the light will follow a generally straight path through the sample cell 130 and will not return to the optical detector 112. Of course, a small amount of the light will pass through the base portion 142 and will be detected by the optical detector 112.

Figure 2C:
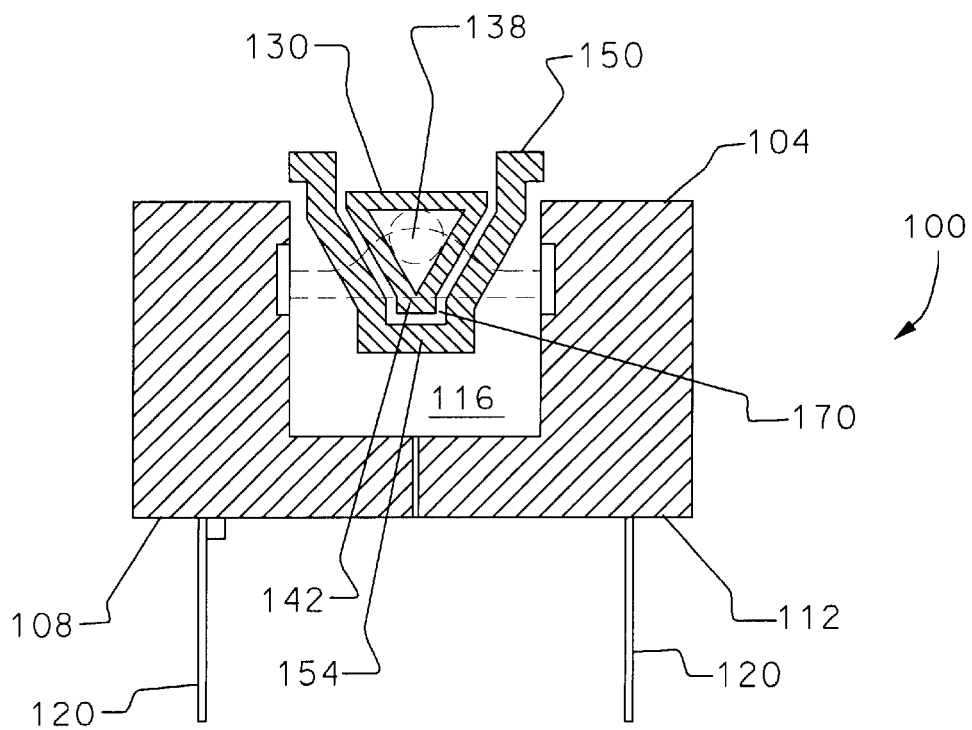
FIG. 2C shows the cross-sectional view of the optical sensing system shown in FIG. 2A, wherein the conduit has an air bubble disposed therein.

Turning now to FIG. 2C, there is shown a similar view to that of FIG. 2A, but with the conduit 138 having a large air bubble disposed therein. The path of the light passing through the base 142 is the same i.e. along plane 2A—2A. The path of the remaining light is the same as FIG. 2A until it reaches the conduit 138. Because air and plastic have significantly different indices of refraction, the light is bent so that it travels generally horizontally across the conduit 138. When the light impacts the opposing portion of the sample cell wall 134b, the light is refracted downwardly. The light is again refracted as it enters and leaves the air chamber 170 and the housing 150, and is directed to the optical detector 112. The amount of light which is received by the optical detector 112 is roughly proportional to the size of the bubble in the conduit 138. Thus, a small bubble will create a small voltage increase, while a large bubble will create a substantial voltage increase. By monitoring the voltage produced by the optical sensor 104, the approximate size of the bubble can be determined. In practical application in an enteral feeding context however, the number of air present signals generated over a given time will generally be more germane. Thus, for example, ten air present signals will indicate that the solution has run dry or has a very high number of air bubbles.

Utilizing the configuration shown, a voltage reading of 0 indicates the sensor is malfunctioning, as some light should be passing through the base portion 142 of the sample cell 130. A reading of 1 volt indicates that the sample cell is full of liquid and that the pump is delivering the indicated volume.

In contrast, a reading of 3–4 volts indicates that a much larger amount of light is being returned than expected, thereby indicating the presence of a bubble. Where the voltage falls within this range indicates the size of the bubble. A reading of 5 volts indicates that the sample cell 130 and housing 150 are not properly mounted in the optical sensor 104 and an alarm is sounded.

By monitoring the number of air bubble signals within a given amount of time, the pump with which the sensor is used can adjust to ensure that the volume of solution delivered to the patient is accurate. If the number of air bubble signals is too high, the pump may shut down and generate an alarm indicating that the solution has run dry or is not properly loaded.

Figure 2D:
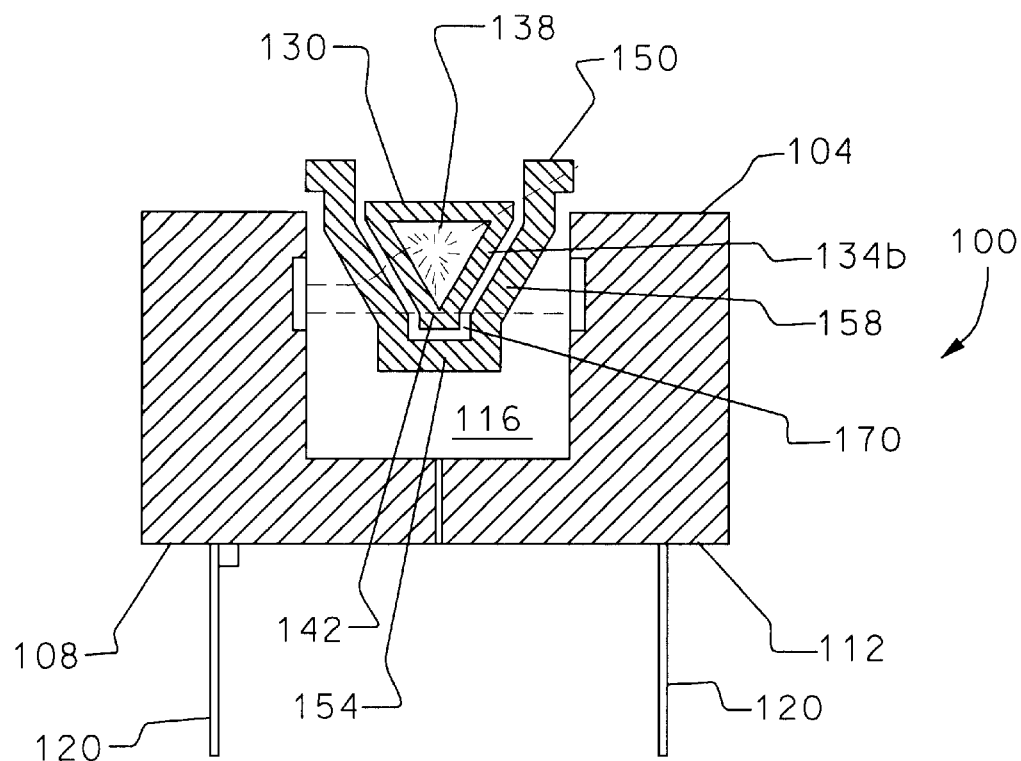
FIG. 2D shows the cross-sectional view of the optical sensing system of FIG. 2 with an opaque solution therein.

Turning now to FIG. 2D, there is shown a cross-sectional view of the sample cell 130 having an opaque solution in the conduit 138. Because the solution is opaque, the light from the optical signal emitter 108 is blocked by the solution in the conduit 138, preventing it from being directed to the optical signal detector 112. Substantially the only light which does reach the optical signal detector 112 is that passing through the base portion 142. Thus, the optical signal detector 112 receives the same signal regardless of whether the sample cell 130 is filled with a transparent solution or an opaque solution. If a large bubble replaces the solution, whether transparent or opaque, the bubble will cause the optical detector 112 to detect more light and indicate the presence of the bubble.

Figure 3:
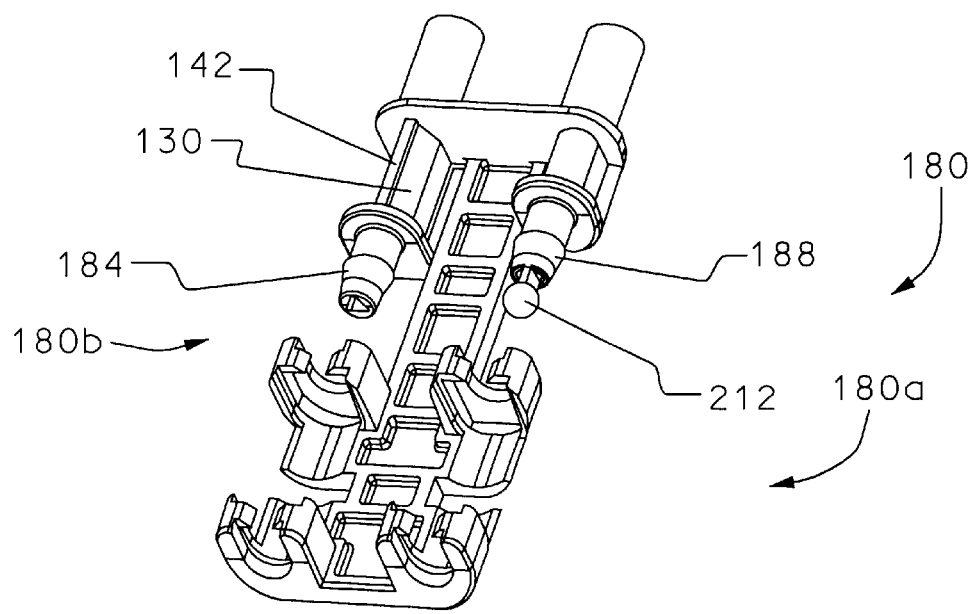
FIG. 3 shows a bottom perspective view of an adaptor for use in enteral feeding pumps having the sample cell of the optical sensor system disposed therein.
Figure 3A:
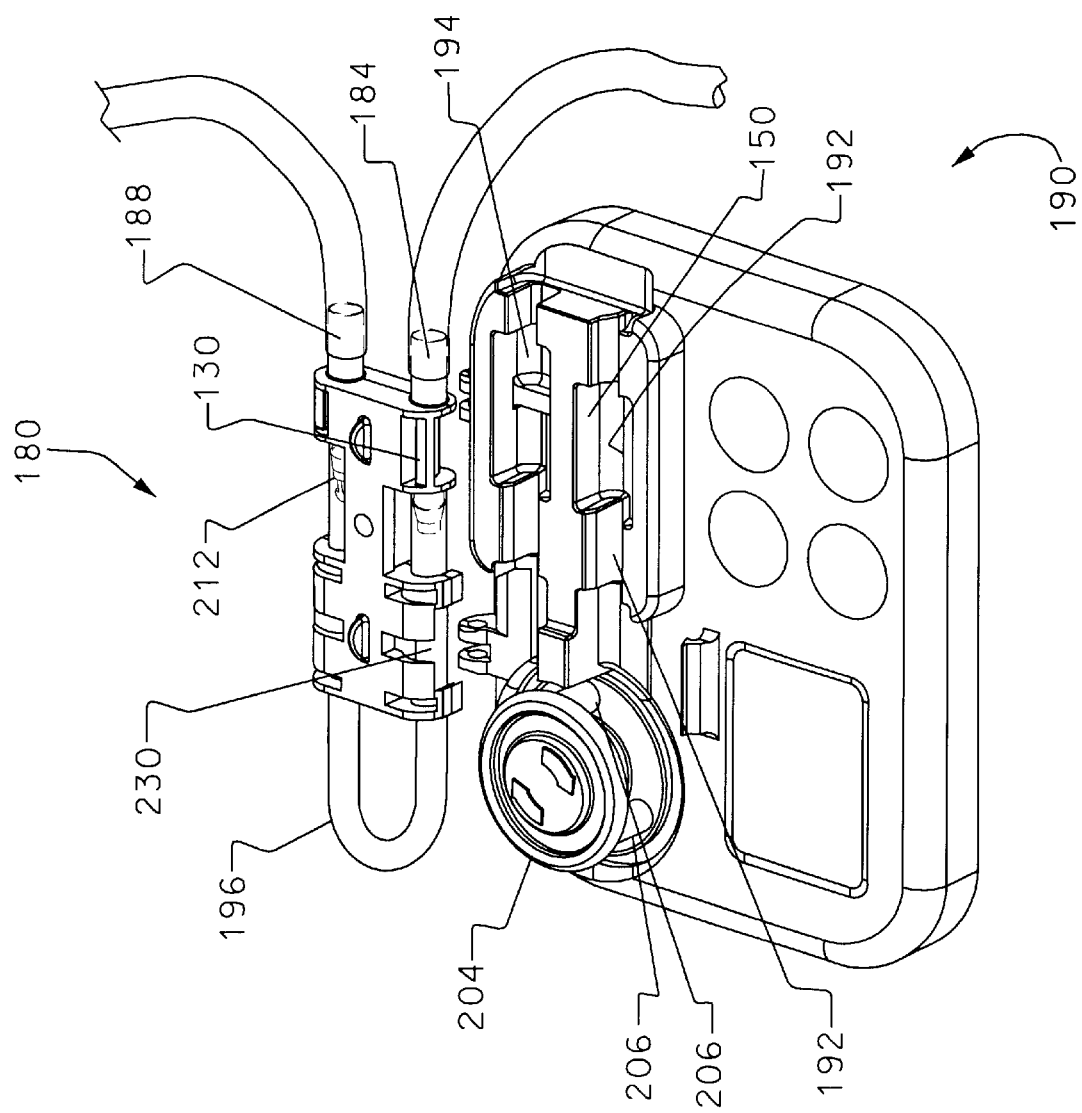
FIG. 3A shows a top perspective view, exploded view of the adaptor and an enteral feeding pump.

Turning now to FIGS. 3 and 3A, there is shown, respectively, a bottom perspective view of an adaptor, generally indicated at 180, and the adaptor 180 in conjunction with a feeding pump 190. The adaptor 180 includes a sample cell 130 of the optical sensor system 104. As shown in FIG. 3, the base portion 142 of the sample cell 130 is disposed on the bottom of the sample cell to allow some light to pass to the optical detector regardless of the contents of the sample cell.

The adaptor 180 enables the sample cell 130 to be conveniently mounted to the enteral feeding pump 190. As explained in additional detail in U.S. patent application Ser. No. 09/836,851 (which is expressly incorporated herein), the pump generally includes a pair of channels 192 and 194 which receive two sides 180a and 180b of the adaptor along with a working portion 196 of an infusion set which is attached at opposing ends to a first connector 184 and a second connector 188.

The sample cell 130 is formed in the first connector and is configured to rest in one channel 192 in the enteral feeding pump 190. The housing 150 (FIGS. 1 through 2D) is typically formed as a wall of the channel 192 associated with the sample cell 130. The optical emitter 108 and the optical detector 112 (not visible in FIG. 3A) are typically disposed on opposing sides of the channel 192 to function in the manner discussed above.

The adaptor 180 also includes an anti-freeflow device 212 configured for positioning in the other channel 194 of the pump 190. Typically, the sample cell 130 and the housing 150 will be disposed upstream, while the anti-freeflow device 212 is typically disposed downstream from a rotor 204 which engages the working portion 196 of the infusion set and moves liquid through the sample cell 130 and past the anti-freeflow device 212 by a plurality of rollers 206 which compress the working portion.

The adaptor 180 enables an infusion set to be quickly loaded into an enteral feeding pump. As the adaptor 180 is pushed into place, the sample cell 130 is automatically positioned between the optical signal emitter 108 and optical signal detector 112 housed in the pump 190. If the pump 190 forms the housing 150, the sample cell 130 will also preferably be positioned away from the channel wall sufficiently to define the air chamber.

If the adaptor 180 is not properly loaded in the pump 190, the amount of light received by the optical signal detector 112 will fall outside a predetermined range. Typically, the optical signal detector 112 will receive much more light than normal, thereby indicating the sample cell 130 is not in place.

Figure 4:
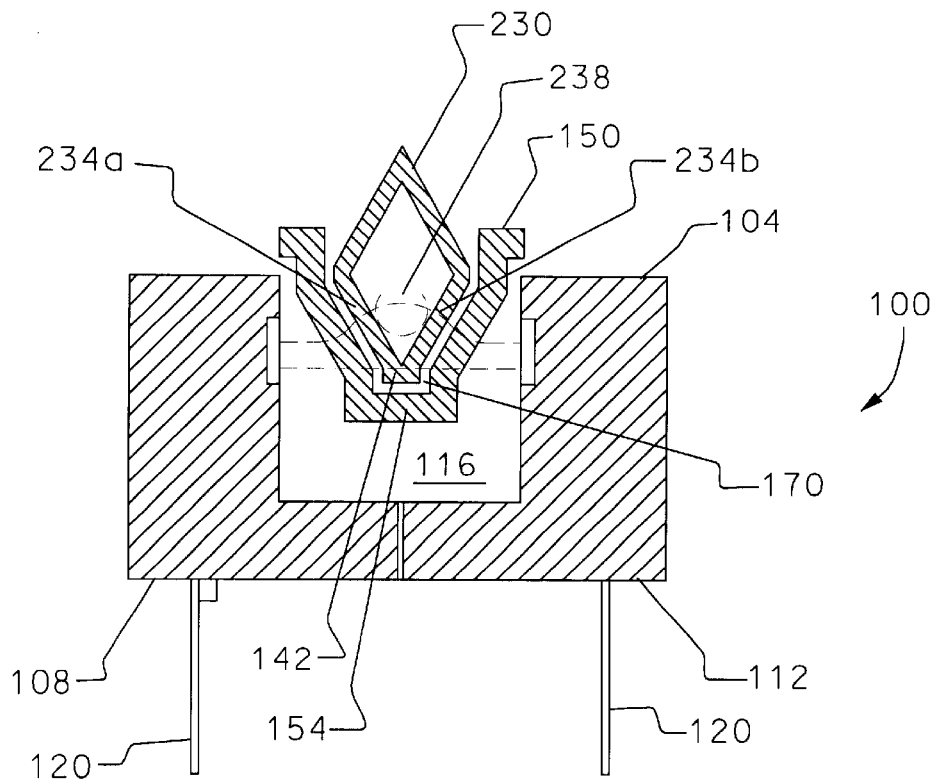
FIG. 4 shows a cross-sectional view of an alternate configuration of a sample cell made in accordance with the principles of the present invention.

Turning now to FIG. 4, there is shown, a cross-sectional view of a sample cell 230 made accordance with the principles of the present invention. While the sample cell 130 forming a conduit with a cross-section which is an inverted equilateral triangle is preferred, such a configuration is not required for the present invention to function properly. Thus, as shown in FIG. 4, the conduit 238 may have a cross-section which is diamond shaped. Because of the angled sidewalls 234a and 234b, are angled between 45 and 100 degrees, and preferably 60 degrees, from one another and are generally the same acute angle from the plane of the light emission, the light follows the same path as discussed above in FIGS. 2B and 2C, thereby enabling the sample cell 230 to be used with the same housing 150 and sensor 104 configuration discussed above. Thus, as shown in FIG. 4, the air bubble in the conduit 238 causes light to be refracted to the optical signal detector 112.

One advantage of the configuration shown in FIG. 4 is that the sample cell 230 will allow a greater amount of solution to flow through the conduit due to its increase in size. Such a configuration, however, may increase the likelihood of a partially filled conduit passing some air which is undetected.

Figure 5:
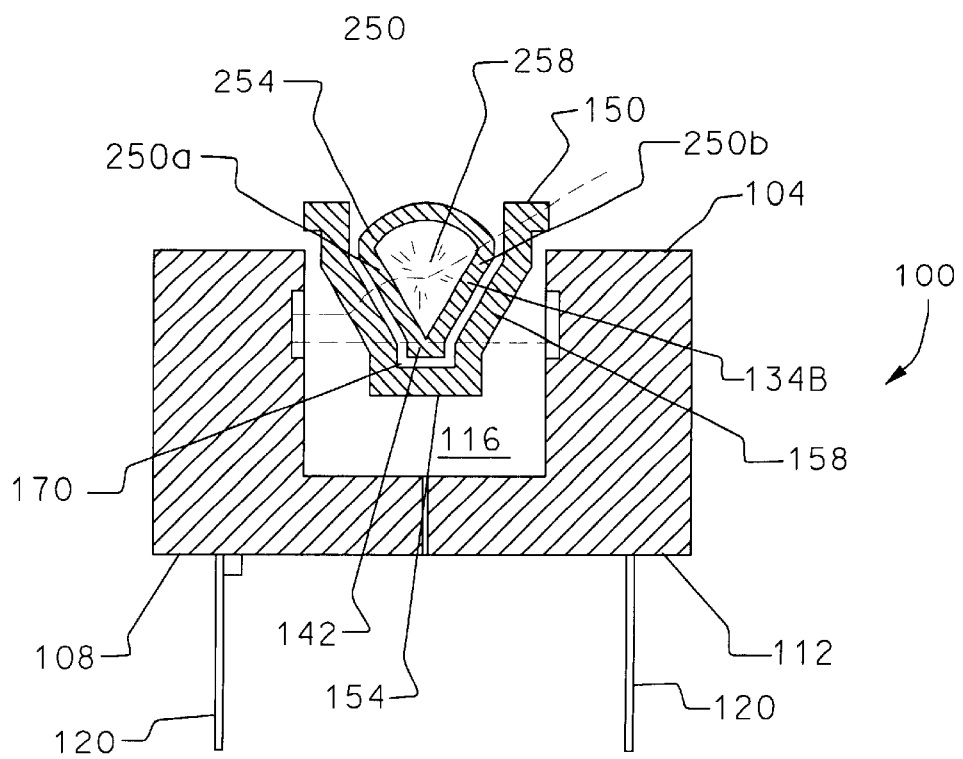
FIG. 5 shows a cross-sectional view of an yet another configuration of a sample cell made in accordance with the principles of the present invention.

FIG. 5 shows a cross-sectional view of another embodiment of a sample cell 250 in accordance with the principles of the present invention. The sample cell 250 has a rounded top wall 254 to allow a greater amount of solution to flow through the conduit 258, while keeping the sidewalls 254a and 254b disposed at an angle between about 45 and 100 degrees, and most preferably about 60 degrees, to provide the desired light refraction when air is present.

Because the most important aspects of the sample cell are the tangential configuration of the sidewalls and the acute angle from the plane of light transmission, those skilled in the art will appreciate that numerous other configurations could be used for forming the conduit. For example, the conduit could have a cross-sectional shape which forms an isosceles triangle, or could form a pentagon or some other shape. In order to properly refract light back to the optical emitter, however, the sidewalls should be separated by an angle between about 45 and 100 degrees, and should have a similar acute angle relative to the plane of light transmission.

Figure 6:
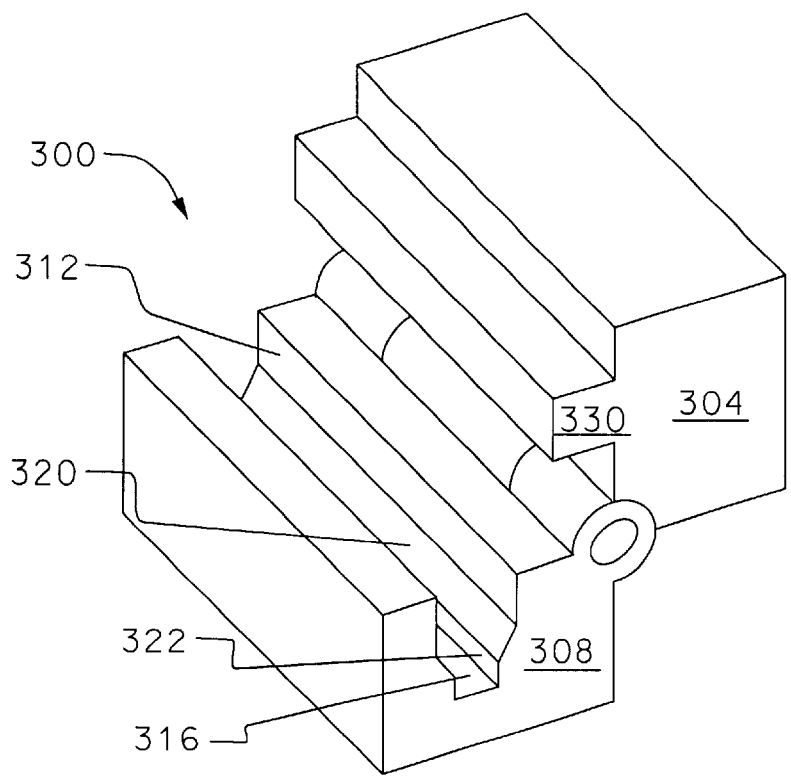
FIG. 6 shows a perspective view of a sample cell container made in accordance with the principles of the present invention in an open position.

Turning now to FIG. 6, there is shown a perspective view of yet another embodiment of a sample cell container, generally indicated at 300, made in accordance with the principles of the present invention. The sample cell container 300 has an upper portion 304 and a lower portion 308 which are engageable one with another. The lower portion 308 has a channel 312 formed therein for receiving a flexible tube. The channel 312 preferably has a base portion 316 for receiving the bottom of the tube and a center portion 320 which is formed by two opposing sloped sidewalls which are preferably sloped downwardly and inwardly toward the base portion at an angle of between about 45 and 100 degrees from each other and with a similar acute angle, i.e. each has the same relative angle with respect to a horizontal plane so that the two would eventually intersect and have an angle between 45 and 100 degrees, and most preferably about 60 degrees.

Figure 6A:
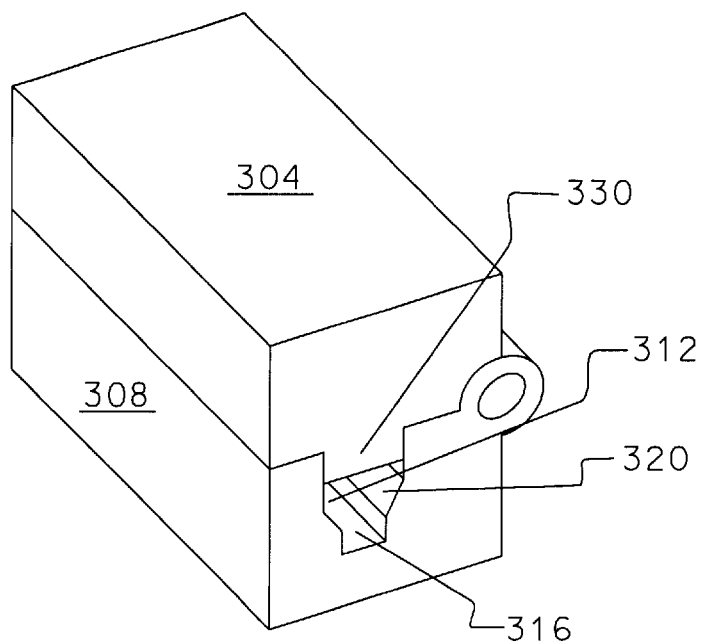
FIG. 6A shows a perspective view of the sample cell container of FIG. 6 in a closed position.

The channel 312 also has a top portion 322 which is configured to receive a protrusion 330 disposed on the upper portion 304. When the upper portion 304 is closed, as shown in FIG. 6A, the protrusion 330 extends down into the channel 312 to force the flexible tube disposed therein into contact with the central portion 320 and base portion 316. This, in turn, causes the flexible tubing to conform to the shape of the channel and form a tube which has a shape similar to that of the sample cell 130 shown in FIGS. 1–2D.

Figure 6B:
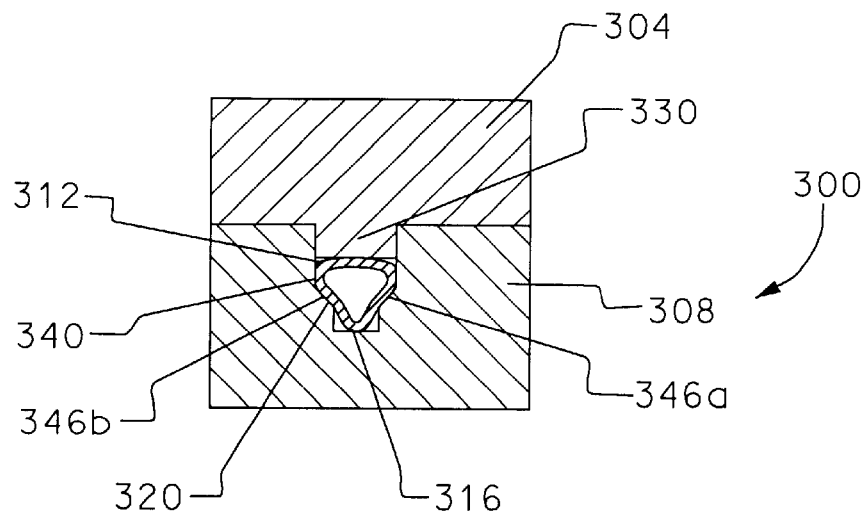
FIG. 6B shows a cross-sectional view of the sample cell container of FIGS. 6 and 6B, forming a sample cell therein.

Turning now to FIG. 6B, there is shown a cross-sectional view of the sample cell container 300 with a flexible tube 340 disposed therein. The protrusion 330 has forced the flexible tube 340 downwardly, wherein the tube substantially conforms to the shape of the channel 312 and has a base portion 342, a central portion having two sidewalls 346a and 346b which are both disposed at the same angle from the horizontal plane, although in opposing directions, and a generally horizontal top portion 346c. In such a manner, the flexible tube 340 forms a sample cell which defines a conduit which is generally triangular. When disposed between an optical emitter and an optical detector, the sample cell formed by the flexible tube 340 will function in substantially the same manner as the sample cell 130 discussed above with respect to FIGS. 1 through 2D.

Those skilled in the art will appreciate that such a configuration is desirable because it allows a conventional infusion set of an enteral feeding pump to be adapted to provide a sample cell in accordance with the principles of the present invention without having to cut the tubing or add an adaptor having a sample cell. Additionally, the sample cell container 300 could be used repeatedly as infusion sets are replaced, thereby keeping cost to a minimum.

Figure 7:
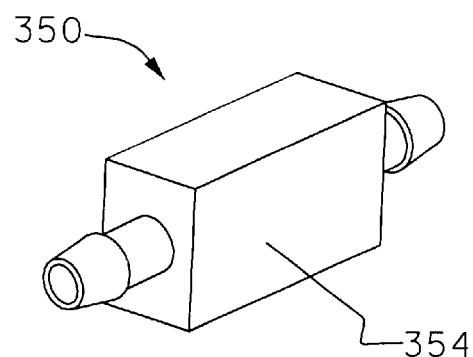
FIG. 7 shows a perspective view of yet another embodiment of a sample cell in accordance with the principles of the present invention.
Figure 7A:
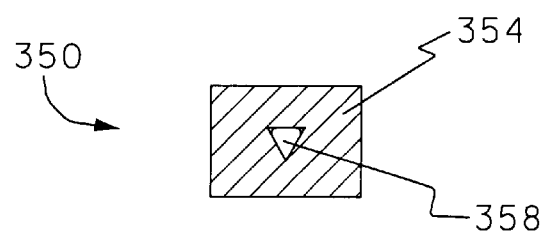
FIG. 7A shows a cross-sectional view of the sample cell of FIG. 7.

Turning now to FIGS. 7 and 7A, there is shown a perspective view and a cross-sectional view of a yet another embodiment of a sample cell of the present invention. The sample cell 350 forms a housing 354 having a rectangular cross-section, and a triangular conduit therethrough. As with the previous embodiments, the conduit 358 has a cross-section which is preferably an equilateral triangle, although other configurations, such as an isosceles triangle, diamond, pie, or other shape will work as well provided that the light refraction is disposed to facilitate different directions of light refraction depending on the contents of the conduit.

Those skilled in the art will appreciate that the configuration shown in FIGS. 7 and 7A are advantageous in that they can be used as a connector for conventional infusion sets for enteral feeding pumps to provide optical bubble detection at minimal cost.

Figure 8:
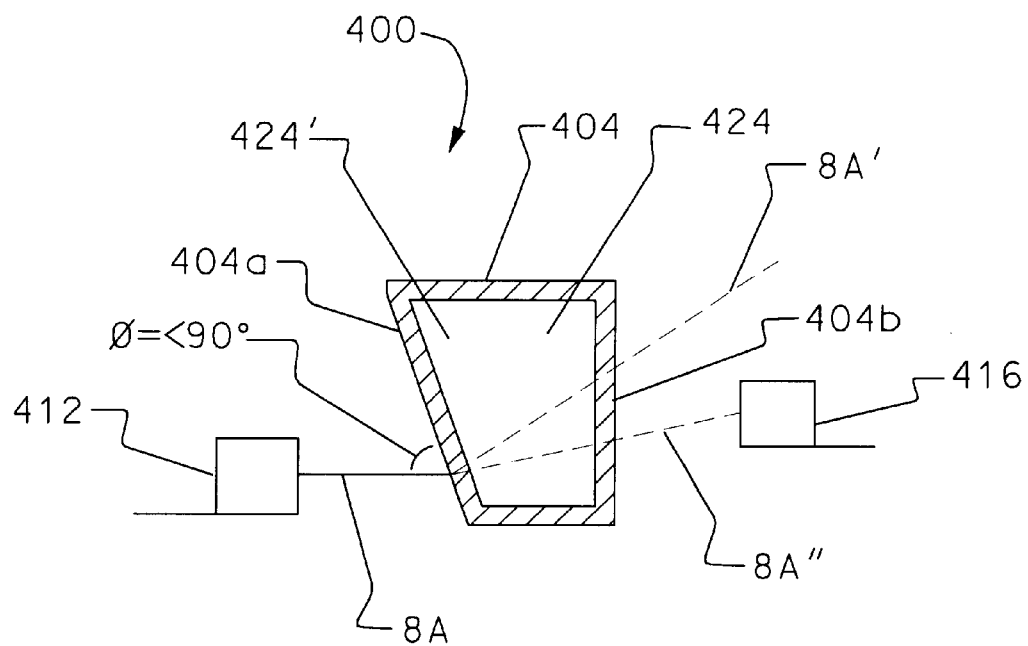
FIG. 8 shows a cross-sectional view of yet another embodiment of the present invention.

While the embodiments discussed above having two sloped sidewalls disposed between 45 and 100 degrees, an in particular about 60 degrees, from one another are a preferred configuration for carrying out the present invention, it has been found that the angles can be much broader while still obtaining some of the benefits of the present invention. As shown in FIG. 8, there is shown a cross-sectional view of a sample cell, generally indicated at 400. The sample cell 400 is: formed by a cell wall 404 which has a first sidewall 404a and the second sidewall 404b.

An optical sensor system, generally indicated at 408 includes an optical emitter 412 and an optical detector 416. The optical emitter 412 emits light (i.e. electromagnetic radiation) along a plane 8A. The optical signal emitter 412 and the sample cell 400 are arranged so that the sidewall 404a Is disposed at an angle less than normal to the plane 8A. As such, the sidewall 404a causes the light to refract as it contacts the outside of the sidewall.

If the sample cell 400 has clear liquid disposed therein, the light undergoes minimal refraction as it passes out of the sidewall 404a, through the liquid 424, and through the opposing sidewall 404b as indicated by plane 8A'. Thus, the light does not reach the optical signal detector 416. Of course, if the liquid disposed in the sample cell 404 is opaque, the liquid will stop the light and prevent it from being received by the optical signal detector 416—giving the same result as a clear liquid.

If an air bubble 424' is disposed in the sample cell 400, the light traveling along plane 8A will be refracted both as it enters and exits the first sidewall 404a, and typically as it enters and exits the second sidewall 404b, so that the light follows plane 8A" and reaches the optical signal detector 416. Thus, even using a relatively small angle in the sample cell wall 404, the light can be directed to the optical signal sensor when air is present, and not when the sample cell is filled with liquid.

While the sample call 400 shown in FIG. 8 has a wall 404a which is less than normal and a wall which is disposed substantially normal to the plane 8A, it will be appreciated that by moving the optical signal emitter 412 and/or the optical signal detector, a variety of different wall configurations, including two less than normal, could be used.

Figure 9:
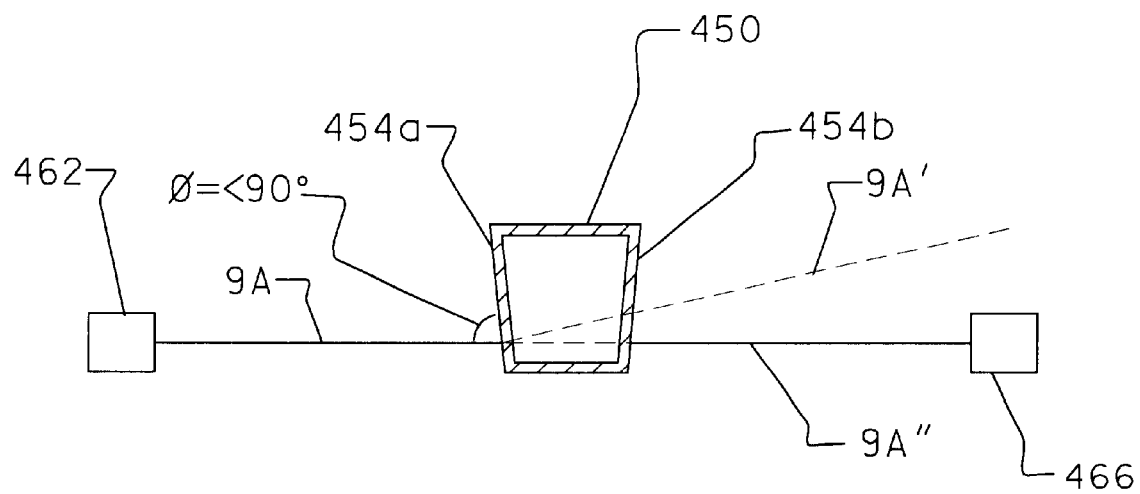
FIG. 9 shows still another embodiment of a sample cell and optical sensor system made in accordance with the principles of the present invention.

Turning now to FIG. 9, there is shown yet another embodiment of a sample cell, generally indicated at 450. The sample cell 450 has a pair of sidewalls 450a and 450b which are disposed slightly off 90 degrees from the plane 9A. The sidewalls 450a and 450b refract light in a manner similar to that discussed above. However, because the angle less than normal (i.e. less than 90 degrees) is so small, the optical signal emitter 462 and the optical signal detector 466 are spaced further from the sample cell 450.

When the light traveling along plane 9A impacts the sidewall 450a it is refracted. If relatively clear liquid is disposed in the sample cell 450, the light follows a relatively straight line, plane 9A' and does not reach the optical signal detector 466. If, however, a predetermined amount of air is present in the sample cell 450, the light is refracted back toward the optical signal detector 466 as it passes from the first sidewall 450 into the conduit 458 in the sample cell, from the conduit into the second sidewall 454b and from the second sidewall back into the air between the sample cell and the optical signal detector. The distance of the optical signal emitter 462 and optical signal detector 466 from the sample cell 450 exaggerates the amount of refraction by providing more distance for the light to travel along the refracted plane.

Thus there is disclosed an improved optical bubble detector. Those skilled in the art will appreciate numerous modifications which can be made to the embodiments and methods discussed herein without departing from the scope and spirit of the present invention. The appended claims are intended to cover such modifications.

What is claimed is:

1. A sample cell for monitoring the flow of a liquid, the sample cell comprising, a cell wall defining a conduit, the conduit having a triangular cross-section, and a base portion positioned adjacent the conduit and along the cell wall, the base portion extending away from the conduit and being configured for the passage of light therethrough without passing through the conduit.

2. The sample cell for monitoring the flow of a liquid according to claim 1, wherein the conduit has a cross-sectional shape of an inverted equilateral triangle.

3. The sample cell for monitoring the flow of a liquid according to claim 1, wherein the cell wall has a generally triangular exterior.

4. The sample cell for monitoring flow of a fluid according to claim 3, wherein the cell wall forms an inverted equilateral triangle.

5. The sample cell for monitoring flow of a fluid according to claim 4, wherein the base portion is positioned at the bottom of the equilateral triangle.

6. The sample cell according to claim 5, wherein sample cell is configured for light to be directed at the sample cell along a path, and wherein at least one side of the base portion forms a wall perpendicular to said path.

7. The sample cell according to claim 1, wherein the base portion extends in a direction transverse to the cell walls defining the conduit.

8. The sample cell according to claim 1, wherein the cell wall has a first wall and a second wall disposed at an angle of between 45 and 100 degrees from one another, and wherein the base portion extends tangentially from both sidewalls.

9. A device for monitoring fluids comprising:
   a sample cell having a cell wall defining a conduit, the cell wall having first and second sidewalls disposed tangentially to ane another, and
   a housing disposed adjacent to, but spaced apart from the sample cell.

10. The device according to claim 6, wherein the housing has a pair of sidewalls disposed in parallel to the sidewalls of the sample cell.

11. The device according to claim 10, wherein the sidewalls of the sample cell and the sidewalls of the housing are disposed at an angle of between about 47 and 70 degrees relative to one another.

12. The device according to claim 11, wherein the sidewalls of the sample cell are offset from one another at an angle of about 60 degrees.

13. The device according to claim 10, wherein the sidewalls of the sample cell and the sidewalls are disposed at an angle of about 60 degrees from a horizontal plane.

14. The device according to claim 9, wherein the housing is spaced from the sample cell to define an air chamber.

15. The device according to claim 9, wherein the housing further comprises an upper flange portion.

16. The device according to claim 9, wherein the housing further comprises a generally horizontal base portion.

17. The device according to claim 16, wherein the housing is formed as a channel wall of an enteral feeding pump.

18. The device according to claim 9, wherein the device further comprises an anti-freeflow mechanism.

19. The device according to claim 9, wherein the device further comprises a cartridge having a tube attached thereto.

20. The device according to claim 9, further comprising an optical emitter and an optical detector.

21. The device according to claim 20, wherein the sample cell has a base portion which is not intersected by the conduit of the sample cell, and which is disposed between the optical emitter and the optical detector for allowing light to be transmitted from the optical emitter to the optical detector regardless of contents in the conduit.

22. The device according to claim 20, wherein the housing has a base portion which is disposed between the optical emitter and the optical detector for allowing light to be transmitted from the optical emitter to the optical detector.

23. The device according to claim 20, wherein the sample cell and the housing each have sidewalls disposed at an angle of about 60 degrees from a plane extending between the optical emitter and the optical detector.

24. A device for monitoring the flow of a liquid, the device comprising:
a sample cell having a cell wall with at least two sidewalls disposed at an angle of between 45 and 100 degrees from one another and defining a conduit;
a housing disposed adjacent to but spaced apart from the sample cell so as to define an air chamber between the housing and the sample cell.

25. The device according to claim 24, further comprising an optical emitter and an optical detector disposed on opposing sides of the housing.

26. The device according to claim 24, wherein the housing has at least two sidewalls disposed substantially parallel to the sidewalls of the cell wall.

27. The device according to claim 24, consisting of a single optical detector.

28. The device according to claim 27, wherein the device comprises means for determining if the sample cell is properly positioned in the housing, means for determining if the optical emitter is working, and means for determining if there is air or liquid in the conduit.

29. The device according to claim 28, wherein the means for determining if the sample cell is properly positioned in the housing, the means for determining if the optical emitter is working, and the means for determining if there is air or liquid in the conduit is the single optical emitter.

30. A bubble detection system comprising the sample cell according to claim 1, and further comprising an optical signal emitter and an optical signal detector.

31. The device according to claim 30, wherein the base portion of the sample cell is disposed to transmit light between the optical emitter and the optical detector uninterrupted by contents of the conduit.

32. A sample cell for use in monitoring of air bubbles in an infusion set, the sample cell comprising a conduit and a base portion extending from the sample cell configured to allow light to pass therethrough regardless of contents of the conduit.

33. The sample cell of claim 32, wherein the sample cell comprises first and second sidewalls disposed tangentially to one another at an angle of between about 45 to 100 degrees.

34. The sample cell according to claim 33, wherein the base portion is configured to allow light to pass therethrough generally horizontally with minimal refraction.

35. An air bubble sensor system comprising a sample cell in accordance with claim 32, further comprising an optical signal emitter and an optical signal detector.

36. The air bubble sensor system according to claim 35, wherein the optical signal emitter is disposed adjacent the first sidewall and wherein the optical signal detector is disposed adjacent the second sidewall.

37. The air bubble sensor system according to claim 36, wherein a light emission plane extends from the optical signal emitter to the optical signal detector, and wherein each sidewall has an acute angle from the light emission plane which is substantially the same as the acute angle from the light emission plane of the other sidewall.

38. The air bubble sensor system according to claim 37, wherein both the first and second sidewalls are disposed 60 degrees from the light emission plane.

39. The air bubble sensor system according to claim 35, further comprising a housing disposed adjacent to the sample cell.

40. The air bubble sensor system according to claim 39, wherein the housing is disposed between the sample cell and the optical signal emitter and the optical signal sensor.

41. The air bubble sensor system according to claim 40, wherein the housing has a sidewall disposed generally parallel to the first sidewall of the sample cell and a second sidewall disposed generally parallel to the second sidewall of the sample cell.

42. The sample cell of claim 32, wherein the sample cell defines a conduit, the conduit having a triangular cross-section.

43. The sample cell according to claim 32, wherein the sample cell defines a conduit and wherein the conduit has a generally diamond shaped cross-section.

44. A method for monitoring a conduit for supplying a liquid, the method comprising:
positioning the conduit between an optical emitter and an optical detector;
emitting a signal from the optical emitter to the optical detector; and
utilizing the optical signal received by the optical detector to determine at least two of the group consisting the presence of the conduit; the presence of air in the conduit; and that optical emitter is sending the optical signal.

45. The method according to claim 44, wherein the method comprises determining that the conduit is in place by detecting an amount of the optical signal less than an amount detected when the conduit is not in place.

46. The method according to claim 44, wherein the method comprises, detecting air in the conduit by detecting an amount of the optical signal received by the optical detector which is greater than the amount received when there is liquid in the conduit.

47. The method according to claim 44, wherein confirmation that the optical emitter is sending an optical signal is determined by the optical detector receiving a portion of the optical signal regardless of whether the conduit is in place and regardless of whether the conduit has air therein.

48. The method according to claim 47, wherein the method comprises passing a portion of the signal through a base portion formed by a wall defining the conduit, the base portion being configured to allow light to pass therethrough with minimal refraction regardless of the contents of the conduit.

49. The method according to claim 44, wherein the method comprises positioning the optical emitter and the optical detector so that the optical detector receives less optical signal when the conduit is in place than when the conduit is not in place, and less optical signal when the conduit is filled with liquid than when the conduit is filled with air.

50. The method according to claim 49, wherein the method comprises positioning the conduit, the optical detector and the optical sensor, so that the optical detector always senses some optical signal from the optical emitter when the optical emitter is working.

51. The method according to claim 44, wherein the method comprises using a single optical detector and optical emitter to determine presence of the conduit, whether the conduit has air therein, and whether the optical emitting is emitting optical signals.

52. A method for monitoring air bubbles in an infusion set, the method comprising;
  selecting a sample cell having a first sidewall and a second sidewall, the first and second sidewall being disposed at an angle relative to one another between about 45 and 100 degrees and having a conduit formed therein;
  transmitting light from an optical signal emitter toward an optical signal detector and into the sample cell and refracting a greater amount of light toward the optical signal detector if air is present in the conduit; and
  directing light through the sample cell such that the optical detector always receives light if the optical emitter is working.

53. The method according to claim 52, wherein the method comprises; more specifically, selecting a sample cell having sidewalls which are offset from one another at an angle of about 60 degrees.

54. The method according to claim 52, wherein the method comprises passing some light from the optical signal emitter to optical signal detector through the sample cell, but not through the conduit.

55. The method according to claim 52, wherein the method further comprises disposing a housing adjacent the sample cell for refracting light.

56. A method for detecting bubbles in a sample cell, the method comprising;
  selecting a sample cell having a conduit, an optical signal emitter and an optical signal detector;
  determining whether the sample cell is properly positioned between the optical signal emitter and the optical signal detector by the amount of light detected by the optical signal detector; and
  causing different amounts of light to be refracted towards the optical signal detector depending, on whether the conduit is filled with air or is filled with a liquid.

57. The method according to claim 56, wherein the method comprises transmitting the light along a plane and refracting the light with a sample cell wall disposed at an angle less than normal to the plane.

58. The method according to claim 56, wherein the method comprises stopping the transmission of light with an opaque liquid in the sample cell.

59. The method according to claim 58, wherein the method comprises directing some light to the optical signal detector regardless of the contents of the sample cell.

60. A method for forming a sample cell from flexible tubing the method comprising:
  selecting a sample cell container having a channel formed therein defining a pair of sidewalls sloping toward one another and being disposed at an angle offset from each other of between about 45 and 100 degrees; and
  engaging the flexible tube with the pair of sidewalls to deform the flexible tube so that the flexible tube has sidewalls disposed generally parallel to the pair of sidewalls of the sample cell container, and so that a base portion is formed for passing light therethrough with minimal refraction.

61. A sample cell container for forming a sample cell from a piece of flexible tubing, the sample cell container comprising;
  a lower portion having a channel formed therein, the channel having a pair of inwardly sloping sidewalls disposed tangentially to one another at an angle of between about 45 and 100 degrees, and a base portion formed at a bottom end of the inwardly sloping sidewalls; and
  an upper portion having a protrusion for nesting into the lower portion to deform the flexible tubing.

62. A method for determining the presence of air in a sample cell, the method comprising;
  selecting a sample cell having a sidewall;
  directing light from an optical emitter along a plane toward the sample cell such that the sidewall of the sample cell is at an angle of less than normal from the plane; and
  selectively refracting the light through the sample cell so that the light is directed to an optical detector when the sample cell is substantially filled with air;
  directing a portion of the light through the sample cell with minimal refraction to indicate that the light has been emitted into the sample cell.

63. The method according to claim 59, wherein the sample cell has a pair of sidewalls through which the light passes, and wherein the sidewalls are angled away from each other at an angle of 45 to 110 degrees.

64. The method according to claim 59, wherein the method comprises positioning the optical sensors to maximize detection of refracted light.

65. A method for monitoring for bubbles, the method comprising;
  selecting a sample cell having a first sidewall and a second sidewall on opposite sides of a conduit;
  passing a portion of the light through the sample cell so that said portion is subject to minimal refraction regardless of the contents of the conduit; and
  refracting light through the first sidewall, the conduit and the second sidewall such that the light reaches an optical signal detector when the sample cell has an air bubble disposed therein, and so that substantially none of the light passing through the conduit reaches the optical detector when the sample cell is filled with liquid.

66. The method according to claim 65, wherein the method comprises, emitting light along a plane, and disposing the first sidewall at an angle less than normal to the plane.

67. The method according to claim 65, wherein the method comprises selecting a sample cell with the first and second sidewalls disposed at an angle between about 45 and 100 degrees from one another.

68. The method according to claim 65, wherein the method further comprises using a single sensor to determine whether light has been emitted and to determine if the sample cell has air herein.

69. The method according to claim 68, wherein the method further comprises refracting a different amount of light to said sensor when the sample cell is in a proper position for monitoring.

\* \* \* \* \*

UNITED STATES PATENT AND TRADEMARK OFFICE
CERTIFICATE OF CORRECTION

PATENT NO. : 6,531,708 B1  Page 1 of 1
APPLICATION NO. : 09/836840
DATED : March 11, 2003
INVENTOR(S) : James A. Malmstrom, Kent F. Beck and Scott D. Miles It is certified that error appears in the above-identified patent and that said Letters Patent is hereby corrected as shown below:

Column 8:
   Line 42, it reads "base portion 342..."; should read --base portion 316...--
   Line 45, it reads "...horizontal top portion 346c."; should read --...horizontal top portion.--

Column 9:
   Line 10, it reads "...100 degrees, an"; should read --...100 degrees, and--
   Line 19, it reads "...system, generally indicated at 408 includes"; should read --...system includes--
   Line 24, it reads "404a Is disposed..."; should read --404a is disposed...--
   Line 46, it reads "While the sample call..."; should read --While the sample cell...--

Column 10:
   Line 2, it reads "first sidewall 450 into the conduit 458 in the..."; should read --first sidewall 454a into the conduit of the...--
   Lines 49-50, it reads "tangentially to ane ..."; should read --tangentially to one...--
   Line 53, it reads "...claim 6, wherein the housing"; should read --...claim 9, wherein the housing--

Column 13:
   Line 9, it reads "...the optical emitting is"; should read --...the optical emitter is--
   Line 25, it reads "method comprises; more..."; should read --method comprises, more...--
   Line 44, it reads "...depending, on whether the"; should read --...depending on whether the--

Signed and Sealed this

Tenth Day of February, 2009

JOHN DOLL
*Acting Director of the United States Patent and Trademark Office*